United States Patent [19]

Tischlinger

[11] 4,072,149
[45] Feb. 7, 1978

[54] NOSE CAP AND DIAPHRAGM ASSEMBLY FOR INJECTOR

[76] Inventor: Edward A. Tischlinger, 7 Froghollow Road, East Lyme, Conn. 06333

[21] Appl. No.: 712,855

[22] Filed: Aug. 9, 1976

[51] Int. Cl.$^2$ .............................................. A61M 5/28
[52] U.S. Cl. ............................................... 128/218 NV
[58] Field of Search .... 128/218 R, 218 NV, 218 DA, 128/221, 215, 216

[56] References Cited

U.S. PATENT DOCUMENTS

| | | | |
|---|---|---|---|
| 2,460,039 | 1/1949 | Scherer et al. | 128/218 NV |
| 3,308,821 | 3/1967 | Shields | 128/218 NV |
| 3,387,609 | 6/1968 | Shields | 128/218 NV |
| 3,391,695 | 7/1968 | Sarnoff | 128/218 NV |
| 3,424,155 | 1/1969 | Sarnoff | 128/218 NV |
| 3,710,794 | 1/1973 | Shields | 128/218 NV |

Primary Examiner—John D. Yasko
Attorney, Agent, or Firm—Y. Judd Azulay

[57] ABSTRACT

A disposable medicament injector having a cylindrical barrel closed at one end by a slidable plunger and at the other end by a nose cap and diaphragm assembly including a flexible and pierceable wall defining a medicament chamber between the plunger and the flexible wall. A spike is positioned in spaced relation to the flexible wall whereby movement of the plunger will cause the medicament in the medicament chamber to flex the flexible wall of the diaphragm toward the spike which will then pierce the flexible wall to establish fluid communication between the medicament chamber and the area on the other side of the flexible wall.

8 Claims, 3 Drawing Figures

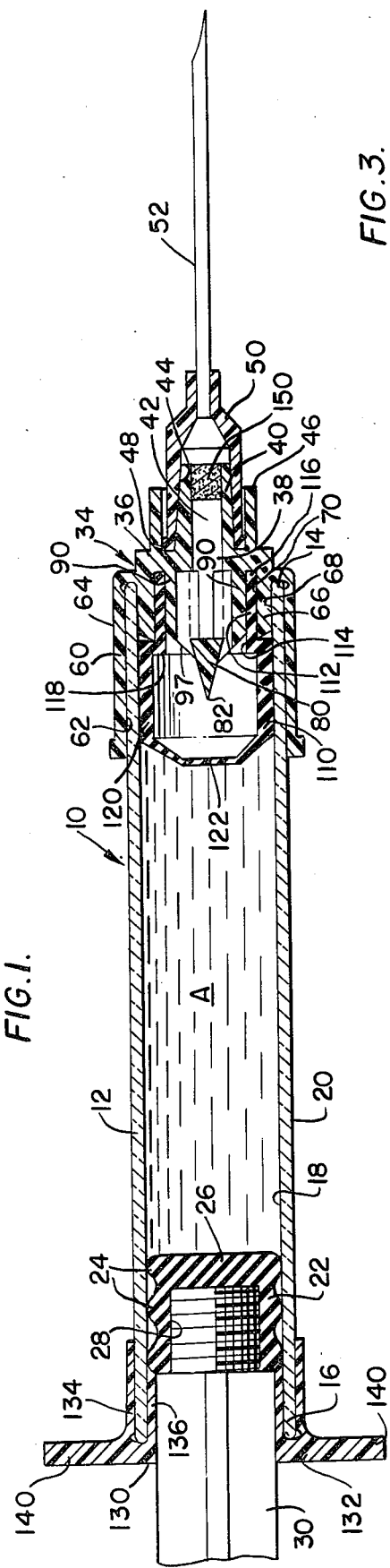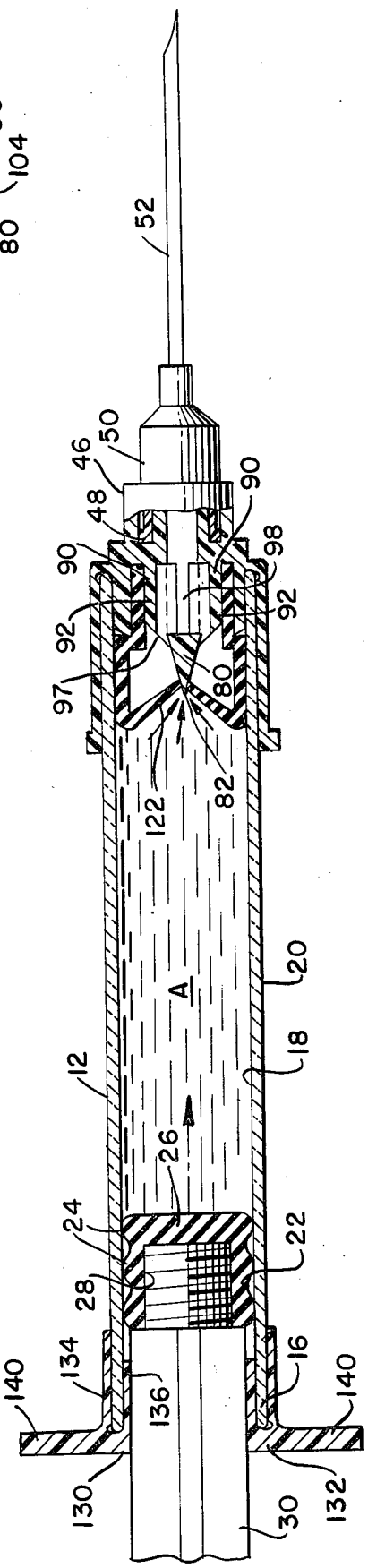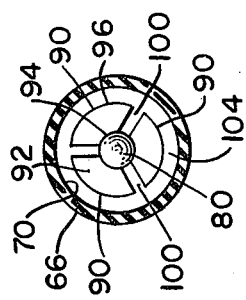

NOSE CAP AND DIAPHRAGM ASSEMBLY FOR INJECTOR

SUMMARY OF THE INVENTION

The field of disposable medicament injectors is quite crowded and yet the needs of the users of such apparatus has not by any means been adequately met. In an effort to provide a disposable medicament injector of great reliability and universal application the injector of this invention has been brought forward.

In view of the foregoing, it is an object of this invention to provide a disposable medicament injector of great reliability and yet extremely simple to use.

It is another object of this invention to provide a disposable medicament injector having a novel nose cap and diaphragm assembly affixed to the injector's cylindrical barrel at the needle end thereof.

It is yet another object of this invention to provide a disposable medicament injector having a medicament chamber formed by a plunger at one end of the injector barrel and a flexible wall at the other end of the barrel with a spike spaced from the flexible wall whereby movement of the plunger toward the flexible wall will cause said flexible wall to flex and be pierced by the spike to establish fluid communication between the medicament chamber and the ambient surroundings.

It is a still further object to provide a nose cap and diaphragm assembly for an injector wherein the assembly comprises a nose cap having a body portion, said body portion being provided with a central bore therethrough which aligns with the longitudinal axis of the injector barrel, the body portion having a forward and a rearward face, means extending forwardly from the body and in fluid communication with the aforesaid bore adapted to mount an injection needle, means extending rearwardly from the body adapted to receive the forward end of the injector barrel, a spike on the rearward side of the body axially aligned with the body bore and having its point directed rearwardly, means for mounting the spike in the aforesaid position, a diaphragm fitted on the rearward side of the body and adapted to seal off the forward end of the injector barrel, said diaphragm including a cylindrical body having one open end, a flexible and pierceable member attached to and closing off the other end of the diaphragm cylindrical body, the diaphragm being fitted into the cap on the rearward side so that the cylindrical body fits around the spike and the closed end is spaced rearwardly from the pointed end of the spike.

The above and additional objects will become more apparent when taken in conjunction with the following detailed description and drawing illustrating a preferred embodiment of this invention.

IN THE DRAWING

FIG. 1 is a longitudinal sectional view of the injector illustrating it in the loaded, ready for use condition;

FIG. 2 is a longitudinal sectional view of the injector illustrating the unit after the plunger has moved forward to flex the diaphragm end wall inwardly for piercing by the spike to allow medicament to flow therethrough, and FIG. 3 is an end elevational view looking into the nose cap with the diaphragm removed to illustrate the means for supporting the spike.

DETAILED DESCRIPTION OF THE INVENTION

As illustrated in FIGS. 1-3, the disposable injector 10 comprises a cylindrical glass barrel 12 having a forward end 14 and a rearward end 16 and an inner surface 18 and an outer surface 20. A rubber plunger 22 is sealingly and slidably carried in the rearward portion of the barrel 12. The plunger 22 is provided with a plurality of circumferential ridges 24 which act as sealing means for the plunger 22 upon engagement with the inner surface 18 of the barrel 12. The forward end of the plunger 22 is closed off by an end face 26 while the rear end has an axially disposed threaded opening 28 adapted to threadedly mount plunger rod 30.

A nose cap and diaphragm assembly is positioned in the forward end of the barrel 12 and comprises a nose cap 34 including a body portion 36 having a central through bore 38 aligned with the longitudinal axis of the barrel 12. A cylindrical projection 40 extends forwardly from the body 34 and has a central passage 42 axially aligned with the body bore 38. The outer surface 44 of the projection 40 is tapered to conform to the conventional Leur taper. A cylinder 46 extends forwardly from the body 34 and spacedly surrounds the projection 40. The cylinder 46 is internally threaded to accommodate mating elements 48 on needle hub 50 mounting needle 52.

An outer sleeve 60 extends rearwardly from body portion 36 and has its longitudinal axis aligned with that of the bore 38. Outer sleeve 60 has an outer surface 64 and a inner surface 62. An inner sleeve 66 having a diameter less than that of outer sleeve 60 extends rearwardly from body 36 and has its longitudinal axis in alignment with that of bore 38. The inner sleeve 66 has an outer surface 68 and an inner surface 70. An annular space is formed between the outer surface 68 of the inner sleeve 66 and the inner surface 62 of the outer sleeve 60, said space receiving the forward end portion of barrel 12.

A spike 80 is positioned rearwardly of body 36 and coaxially with the longitudinal axis of outer sleeve 60. The spike 80 is conical in shape with its point 82 directed rearwardly and terminating short of the rearward edge of the outer sleeve, 60. The spike is mounted within the sleeve 60 by means of three segmental supports 90 which extend rearwardly from the body 36. More specifically, each segmental support 90 comprises a longitudinal body 92 having inner and outer body surfaces 94 and 96 corresponding in curvature to that of the inner surface 70 of inner sleeve 66. The longitudinal bodies 92 are sized such that when the three bodies are equidistantly positioned around the axis of the sleeve 60 a small passage 98 is formed to provide fluid communication between the area surrounding the spike 80 and the body bore 38. In such arrangement there is a space between each adjacent body 92 to complete the aforesaid fluid communication. The outer surfaces 96 of the longitudinal bodies 92 and adjacent inner surface 70 of the inner sleeve 66 form an annular space 104 adapted to receive a portion of the diaphragm to be described next.

Diaphragm 110 comprises a cylindrical base 112 having an upper end 114 and lower end 116. A flange 118 extends radially outward from the upper end 114 of the base 112 with a cylindrical wall 120 extending upwardly from the periphery of the flange 118. The upper end of the wall 120 is closed off by a flexible wall 122 having a reduced thickness to aid in flexibility and pierceability.

As previously stated, the diaphragm base 112 fits into space 104 formed by the inner surface 70 of inner sleeve 66 and the segmented surface formed by support body outer surfaces 96. It should be noted that the end faces 97 of the supports 90 slope downwardly and outwardly to aid in the insertion of the diaphragm body into space 104.

A finger grip 130 is mounted on the rear end of the barrel 12 and includes a grip body 132 having an outer sleeve 134 and an inner sleeve 136 extending outwardly therefrom in spaced manner to form an annular space into which the rear end of the barrel 12 fits. Finger grips 140 extend radially outward from the body 132.

In normal storage condition, the unit is stored without the plunger rod 30 and the needle 52. When readying for use, the plunger rod 30 is affixed to the plunger 22 and the needle 52 is assembled to the nose cap 34. After the needle 52 is inserted into the locus to receive the medicament forward movement of the plunger 22 causes diaphragm wall 122 to contact the point 82 of the spike 80 and to be pierced thereby so as to provide fluid communication between the medicament chamber A and the needle 52. Central passage 42 of the projection 40 may be provuded with a sintered metal filter 150 if desired.

What is claimed is:

1. A nose cap and diaphragm assembly for use in an injector including a cylindrical barrel closed at its rearward end by a slidable plunger and at its forward end by the nose cap and diaphragm assembly, said assembly comprising:
   a nose cap, said nose cap having a body portion, said body portion having a central bore therethrough which aligns with the longitudinal axis of the barrel when the nose cap is assembled on the forward end of said barrel, the body portion having a forward and a rearward face, means extending forwardly from the body and in fluid communication with the aforesaid bore adapted to removably receive and mount an injection needle, means extending rearwardly from the body adapted to receive the forward end of the cylindrical barrel, a spike distinct from any injection needle that might be mounted on the forward needle mounting means on the rearward side of the body axially aligned with the body bore and having its point directed rearwardly, means for mounting the spike in such axial alignment, and
   a diaphragm fitted on the rearward side of the body portion and adapted to seal off the forward end of the cylindrical barrel, said diaphragm comprising a cylindrical body having one open end, a flexible and pierceable member attached to and closing off the other end of this cylindrical body, the diaphragm being fitted into the nose cap on the rearward side so that the cylindrical body fits around the spike and the closed end is spaced rearwardly therefrom.

2. A nose cap and diaphragm assembly for use in connection with an injector including a cylindrical barrel closed at one end by a slidable plunger end at the other end by said nose cap and diaphragm assembly comprising:
   a nose cap, said nose cap having a body portion, said body having a central throughbore, a generally cylindrical projection extending forwardly from said body portion coaxially with the central throughbore, a sleeve extending forwardly from said body portion and spaced outwardly from the projection to provide an annular space to removably receive the hub portion of an injection needle, a cylindrical outer sleeve extending rearwardly from the body portion, a cylindrical inner sleeve extending rearwardly from said body portion and spaced radially inward from the outer sleeve, the inner and outer sleeves defining a space adopted to receive one end portion of the cylindrical barrel, a spike distinct from any injection needle that might be mounted on the generally cylindrical needle mounting means, said spike being centrally and axially positioned with respect to the outer sleeve with its point facing rearwardly, means for supporting the spike whereby fluid communication is provided between the spike and the projection extending forwardly from the body, and
   a diaphragm fitted within the rearward portion of the nose cap and comprising:
   a cylindrical base having an upper and lower end, a flange extending radially outward from the upper end of the base, a cylindrical sleeve extending axially from the periphery of the flange in an upward direction, and a flexible and pierceable member closing off the upper end of said cylindrical sleeve, said diaphragm being fitted within the nose cap so that the flexible and pierceable member is spaced rearwardly of the spike point whereby the diaphragm acts as a seal to close off said forward end of the injector barrel.

3. A disposable medicament unit comprising:
   a cylindrical barrel having inner and outer surfaces and open on both its front and rear ends, a plunger slidably carried in the rear end of the barrel in sealing relation to the inner surface of the barrel, and a nose cap and diaphragm assembly fixedly mounted on and closing off the front end of the barrel, said assembly forming a medicament chamber between the plunger and the diaphragm, the nose cap comprising a body portion, said body portion having a central bore therethrough which aligns with the longitudinal axis of the barrel when the nose cap is assembled on the front end of said barrel, the body portion having a front and a rear face, means extending frontward from the body and in fluid communication with the aforesaid bore to removably receive and mount an injection needle, means extending rearwardly from the body to receive the forward end of the cylindrical barrel, a spike distinct from any injection needle that might be mounted on the forward needle mounting means on the rearward side of the body axially aligned with the body bore and having its point directed rearwardly, means for mounting the spike in the aforesaid position, a diaphragm fitted on the rearward side of the body and sealing off the forward end of the barrel, said diaphragm including a flexible and pierceable wall having a front and a rear face, the front face thereof being spaced rearwardly of the spike point whereby when the plunger moves frontward the flexible wall will be flexed frontward to engage and be pierced by the spike to establish fluid communication between the medicament chamber and the front side of the diaphragm.

4. The invention as set forth in claim 3 and wherein the nose cap is a unitary structure.

5. The invention set forth in claim 3 and wherein the diaphragm comprises a cylindrical body having one open end, a flexible and pierceable wall having a front and rear face attached to and closing off the other end of the cylindrical body.

6. The invention as set forth in claim 3 and wherein the diaphragm comprises a cylindrical base having an upper and a lower end, a flange extending radially outward from the upper end of the base, a cylindrical sleeve extending axially from the periphery of the flange in an upward direction, a flexible and pierceable wall having a front and a rear face closing off the upper end of the cylindrical sleeve.

7. The invention as set forth in claim 3 and wherein the spike is cone shaped.

8. The invention as set forth in claim 6 and pierceable wall of the diaphragm has a thickness less than that cylindrical base and the cylindrical sleeve.

* * * * *